(12) United States Patent
Sahin et al.

(10) Patent No.: US 11,123,432 B2
(45) Date of Patent: Sep. 21, 2021

(54) ANTIMICROBIAL INSECT REPELLENT COMPOSITION

(71) Applicant: YEDITEPE UNIVERSITESi, Istanbul (TR)

(72) Inventors: Fikrettin Sahin, Istanbul (TR); Zeynep Iyigundogdu, Istanbul (TR); Okan Demir, Istanbul (TR); Sadik Kalayci, Istanbul (TR); Binnur Kiratli, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 0 days.

(21) Appl. No.: 16/463,407

(22) PCT Filed: Nov. 8, 2017

(86) PCT No.: PCT/TR2017/050557
§ 371 (c)(1),
(2) Date: May 23, 2019

(87) PCT Pub. No.: WO2019/032061
PCT Pub. Date: Feb. 14, 2019

(65) Prior Publication Data
US 2019/0351059 A1    Nov. 21, 2019

(30) Foreign Application Priority Data

Nov. 23, 2016    (TR) .................................. 2016/17080

(51) Int. Cl.
*A61K 47/10*    (2017.01)
*A61P 31/10*    (2006.01)
(Continued)

(52) U.S. Cl.
CPC .............. *A61K 47/10* (2013.01); *A01N 25/22* (2013.01); *A01N 37/18* (2013.01); *A01N 59/00* (2013.01);
(Continued)

(58) Field of Classification Search
None
See application file for complete search history.

(56) References Cited

U.S. PATENT DOCUMENTS

2008/0305071 A1    12/2008   Lloyd et al.
2011/0262508 A1*   10/2011   Watt ........................ C07K 14/00
                                                        424/405

(Continued)

FOREIGN PATENT DOCUMENTS

CN    103864511 A  *  6/2014
KR    101560491 B1 *  10/2015
(Continued)

OTHER PUBLICATIONS

Lalitha M. K. et al., 'Manual on Antimicrobial Susceptibility Testing',URL: http://www.ijmm.org/documents/Antimicrobial.doc, 2005.

(Continued)

*Primary Examiner* — Kyung S Chang
(74) *Attorney, Agent, or Firm* — Bayramoglu Law Offices LLC

(57) ABSTRACT

An antimicrobial (anticandidal, antibacterial, antifungal) and antiviral composition which repels insects such as flies, mosquitoes and ticks. The composition includes poloxamer, boron compound, ethyl butyl acetylaminopropionate and preferably hydrogen peroxide. The present composition is a composition which can be applied in different forms via oral, (Continued)

nasal, ophthalmic, otic, local, ventricle, vaginal, rectal, dermal, intravenous, intramuscular, subcutaneous and intradermal route.

6 Claims, 2 Drawing Sheets

(51) Int. Cl.
| | | |
|---|---|---|
| A61P 31/04 | (2006.01) |
| A61K 33/40 | (2006.01) |
| A61K 33/22 | (2006.01) |
| A01N 25/22 | (2006.01) |
| A01N 37/18 | (2006.01) |
| A01N 59/00 | (2006.01) |
| A01N 59/14 | (2006.01) |
| A61K 31/221 | (2006.01) |
| A61P 31/20 | (2006.01) |

(52) U.S. Cl.
CPC ............ *A01N 59/14* (2013.01); *A61K 31/221* (2013.01); *A61K 33/22* (2013.01); *A61K 33/40* (2013.01); *A61P 31/04* (2018.01); *A61P 31/10* (2018.01); *A61P 31/20* (2018.01)

(56) References Cited

U.S. PATENT DOCUMENTS

| | | | |
|---|---|---|---|
| 2013/0149278 A1 | 6/2013 | Lloyd et al. | |
| 2018/0020661 A1* | 1/2018 | Termer | A01N 65/44 514/551 |

FOREIGN PATENT DOCUMENTS

| | | | |
|---|---|---|---|
| WO | 2014168592 A1 | 10/2014 |
| WO | 2014168595 A1 | 10/2014 |
| WO | 2016124306 A1 | 8/2016 |

OTHER PUBLICATIONS

Katz, T. M. et al. Insect repellents: Historical perspectives and new developments. J. Am. Acad. Dermatol. May 2008, 58 (5), 865-871.
Brown M et al. Insect repellents: An overview. Journal of the American Academy of Dermatology, Feb. 1997; 36 (2): 243-9.
Mustapha Debboun et al. Insect Repellents Principles, Methods, and Uses. London. CRC Press, 2006: 397-402.
Bissinger BW et al. Tick Repellents: Past, Present, and Future. Pesticide Biochemistry and Physiology, Oct. 1, 2009; 96: 63-79.
Osimitz T.G. et al . . . Adverse Events Associated with the Use of Insect Repellents Containing N,N-Diethyl-M-Toluamide (Deet). Regulatory Toxicology and Pharmacology, 2010; 56: 93-99.
Costanzo SD, et al. Is There a Risk Associated with the Insect Repellent Deet (N,N-Diethyl-M-Toluamide) Commonly Found in Aquatic Environments? Science of the Total Environment, 2007; 384: 214-20.
Uccetti G. IR3535 (Ethyl Butylacetylaminopropionate). In: Debboun M, Frances SP, Strickman D, eds. Insect Repellents Principles, Methods, and Uses. 2006, pp. 353-360 London. CRC Press.
Kalayci S., et al. Antimicrobial Properties of Various Psychotropic Drugs Against Broad Range Microorganisms. Current Psychopharmacology, 2014, vol. 3 No. 3, pp. 195-202.
Bailey P. J., et al. Boron-Containing Antibacterial Agents: Effects on Growth and Morphology of Bacteria Under Various Culture Conditions. Antimicrobial Agents and Chemotherapy, vol. 17, No. 4, Apr. 1980, p. 549-553.
Benkovic S.J., et al. "Identification of Borinic Esters as Inhibitors of Bacterial Cell Growth and Bacterial Methyltransferases, CcrM and MenH". Journal of Medicinal Chemistry. 48:7468-7476, 2005.
Reynolds, R.C., et al. Novel Boron-containing, Nonclassical Antifolates: Synthesis and Preliminary Biological and Structural Evaluation. Journal of Medicinal Chemistry, 50:3283-3289, 2007.
Qin G., et al. Crucial Role of Antioxidant Proteins and Hydrolytic Enzymes in Pathogenicity of Penicillium Expansum, Molecular & Cellular Proteomics, 6:425-438, 2007.
Qin G., et al. "Inhibitory Effect of Boron against Botrytis Cinerea on Table Grapes and Its Possible Mechanisms of Action", International Journal of Food Microbiology 138:145-150, 2010.
Batrakova, Elena V. et al. "Pluronic Block Copolymers: Evolution of Drug Delivery Concept from Inert Nanocarriers to Biological Response Modifiers." Journal of Controlled Release 130.2, 98-106, 2008.
Kabanov, Alexander V., et al. Micelle Formation and Solubilization of Fluorescent Probes in Poly (oxyethylene-b-oxypropylene-b-oxyethylene) Solutions. Macromolecules 28.7, 2303-2314, 1995.
Ramirez, Octavio T. et al. The Role of the Plasma Membrane Fluidity on the Shear Sensitivity of Hybridomas Grown under Hydrodynamic Stress. Biotechnology and Bioengineering. 1990 vol. 36. No. 9, pp. 911-920.

\* cited by examiner

ANTIMICROBIAL INSECT REPELLENT COMPOSITION

CROSS REFERENCE TO THE RELATED APPLICATIONS

This application is the national phase entry of International Application No. PCT/TR2017/050557, filed on Nov. 8, 2017, which is based upon and claims priority to TR Patent Application No. 2016/17080, filed on Nov. 23, 2016, the entire contents of which are incorporated herein by reference.

TECHNICAL FIELD

The present invention relates to an antimicrobial (anticandidal, antibacterial, antifungal) and antiviral composition which repels insects such as flies, mosquitoes and ticks.

BACKGROUND

Repellent molecules are the name given to substances which are directly applied on humans or pets or on their clothing and which repel creatures such as flies, mosquitoes, ticks, etc. As a result of the studies conducted, the most important properties sought in repellent molecules are having broad spectrum activity on many arthropods and not being toxic-allergenic. When they are applied on the skin, they should not be causing irritation dermatologically. Furthermore it should maintain its activity for a long period of time and should not cause change of color in clothes. The first synthetic repellents were researched during World War 2 mainly by the United States army for protecting the military troops. In those years, repellence of thousands of compounds was studied. However, very few of those found commercial use.

Deet (N,N-Diethyl-meta-toluamide), which is one of the most well-known repellents, is a molecule that was developed by the United States army in 1946 for protecting the soldiers and was introduced into the market in 1957. The studies conducted so far have shown that Deet is the most effective repellent molecule on biting flies, mosquitoes and ticks. The Deet concentrations in the commercially available products vary between 5% and 100%. Upon formulation of Deet, many repellent molecules (Dimethyl phthalate, Indalon, Ethyl hexanediol) which were used previously lost their importance. Although repellence of over 20,000 substances was examined until today, none of them achieved a success comparable to Deet. Use of Deet per year in the United States amounts to 1.8 million kg.

Ethyl Butyl acetylaminopropionate or EBAAP is naturally synthesized from b-alanine and due to structural similarity to the main compound, it is registered as a biopesticide by EPA. Although EBAAP has been used as a repellent in Europe since 1970's, it was permitted to be used in the United States only in 1999. Today, spray and lotion formulas thereof are widely used.

As a result of many toxicity experiments, it was accepted that EBAAP does not cause irritation on the skin and that it is generally safe. In fact, it causes much less irritation at the mucosas and has low oral and dermal toxicity compared to Deet which is the most widely used repellent. It was also approved for use by WHO in 2001. According to the researches conducted, antimicrobial and antiviral properties of EBAAP have not been studied yet.

There are studies in the state of the art on the antimicrobial properties of some boron compounds. Bailey et al. (1980) found, with the experiments they conducted, that boric acid has antibacterial activity on enteric bacteria. Antimicrobial agents containing boron were tried on gram negative bacteria (*Escherichia coli* and *Proteus mirabilis*) and were observed to be effective.

Additionally, in a study by Benkovic et al (2005), it was observed that boric esters have a broad spectrum antibacterial activity. Results of their study reveal that boric esters inhibit DNA methyl transferase in gram negative and positive bacteria.

Reynold et al. (2007) indicated that lipophilic 2,4-diamino-6-methylpyrimidine antifolate compound, which comprises two different borons, has a moderate level antibacterial activity against the bacteria *Mycobacterium avium* and *Lactobacillus casei*. In addition, it is shown that some boron derivatives have antifungal activities.

A study by Qin et al. (2007) showed that potassium tetraborate has an inhibitory effect on micelle growth of *Penicillium expansium*. It was indicated that 0.1% concentration of potassium tetraborate is the minimum concentration preventing micelle growth. Qin et al. (2010) also searched for the effects of potassium tetraborate on *Botrytis cinerea* which is the pathogen leading to gray mold disease. They showed that they could control this mold causing disease on the grapes by using potassium tetra borate with 1% concentration.

Poloxamers are synthetic polymers which have a triblock structure composed of hydrophobic polypropylene oxide and hydrophilic polyethylene oxide units. Poloxamer can be used for carrying therapeutic agents, drugs and genes. Due to their amphiphilic structures, they are surfactant and can interact with membranes. They can be used in bioreactors for enhancing cell viability and decreasing agitation stress. Different components of poloxamers are used in nanogel formulation. Thanks to mucoadhesive properties of these polymers, the drug can effectively penetrate into the cell and its efficacy can be enhanced by preventing decomposition thereof.

United States patent document no. US2013149278 discloses a boron containing composition for insect control.

United States patent document no. US2008305071 discloses an antimicrobial boron-containing insect repellent cleaning product.

SUMMARY

An objective of the present invention is to provide an antifungal composition.

Another objective of the present invention is to provide an anticandidal composition.

Another objective of the present invention is to provide an antibacterial composition.

Another objective of the present invention is to provide an antiviral composition.

Another objective of the present invention is to provide an insect repellent (flies, mosquitoes and ticks) composition.

A further objective of the present invention is to provide a composition which can be applied on lotions, creams, gels, aerosols, textile surfaces, hygienic products.

Another objective of the present invention is to provide a composition which can be applied on all kinds of surfaces.

Another objective of the present invention is to provide a composition which prevents biodegradation or biocontamination.

A further objective of the present invention is to provide a composition which enables to control pathogen microorganisms and agents causing allergic and infectious diseases and to reduce potential diseases.

BRIEF DESCRIPTION OF THE DRAWINGS

"An Insect Repellent Composition" developed to fulfill the objectives of the present invention is shown in the accompanying figures wherein.

DETAILED DESCRIPTION OF THE EMBODIMENTS

Experimental Studies

Figure 1:
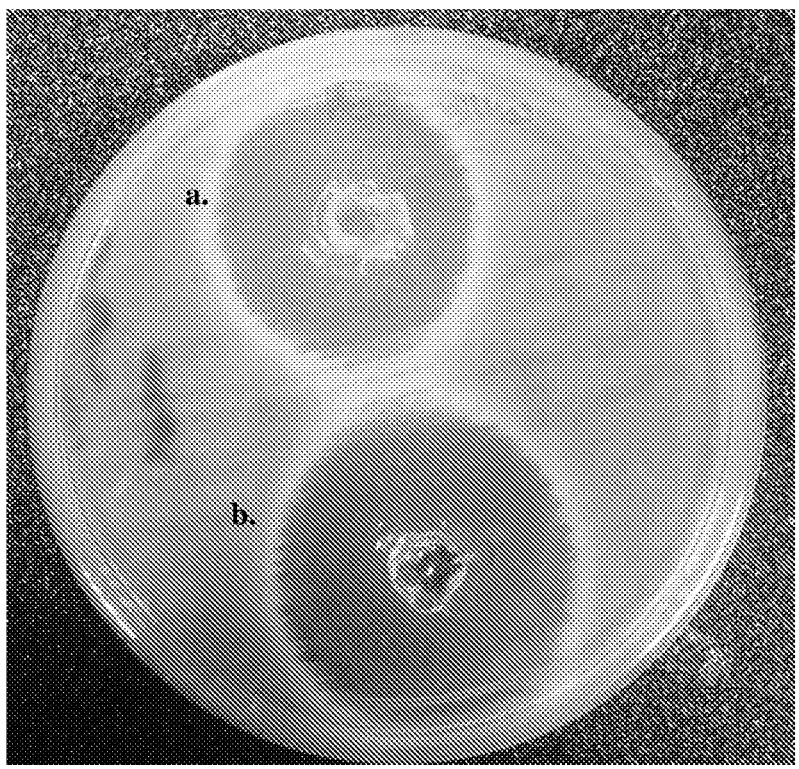
FIG. 1 shows a view of the antifungal activity of the EBAAP (Ethyl Butyl Acetylaminopropionate) and Sodium borate containing composition comprising 5% poloxamer (reference "a") and 3% poloxamer (reference "b") respectively against *Aspergillus niger*.
Figure 2:
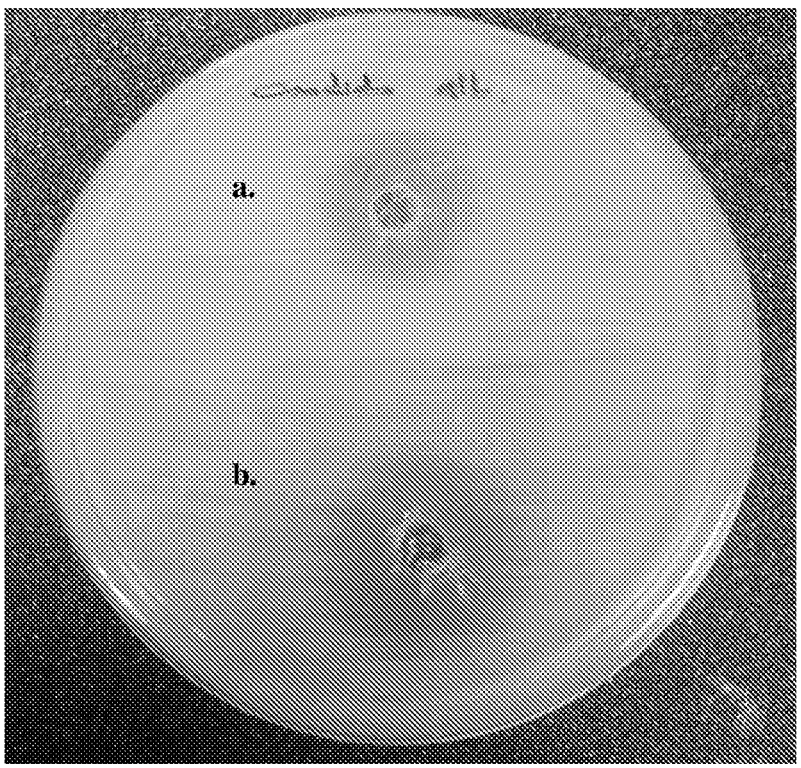
FIG. 2 shows a view of the anticandidal activity of the composition containing EBAAP and Sodium borate containing composition comprising 5% poloxamer (reference "a") and 3% poloxamer (reference "b") respectively against *Candida albicans*.
Figure 3:
FIG. 3 shows a view of the anticandidal activity of the EBAAP and Sodium borate containing composition comprising 5% poloxamer (reference "a") and 3% poloxamer (reference "b") respectively against *Staphylococcus aureus*.

By means of the present invention, compositions of different concentrations and combinations which contain boron compounds, EBAAP (Ethyl Butylacetyl Aminopropionate), hydrogen peroxide and poloxamer separately or together.

In the present invention; one of sodium pentaborate pentahydrate, zinc borate, disodium octaborate tetrahydrate, sodium borate, sodium perborate tetrahydrate, borax pentahydrate, and preferably sodium borate is selected as the boron compound.

Preparation of the Combination

Composition-1

The gel, which is a carrier for the active molecules, was prepared by using 1-15% (w/w) poloxamer. In preparation of the gel, first of all 15-25% (w/w) EBAAP was added to an amount of distilled water that will be used in the formulation, then 1-10% (w/w) poloxamer was added to this mixture and the resulting mixture was allowed to rest at +4° C. until poloxamer precipitated (approximately 24 hours). After poloxamer precipitated, the mixture was homogenized by the help of a homogenizer or a stirrer, and then upon adding 1-5% (w/w) sodium pentaborate pentahydrate, it was allowed to hydrate at +4° C. After jelling is completed, if considered necessary, sodium carbonate or citric acid can be used for neutralizing pH. The mixture became ready for use upon being allowed to rest at +4° C. for 24 hours. After formation of gelling, the composition of the invention is in gel form.

Composition-2

The gel, which is a carrier for the active molecules, was prepared by using 1-15% (w/w) poloxamer. In preparation of the gel, first of all 1% (w/w) hydrogen peroxide ($H_2O_2$) was added to distilled water in an amount that will be used in the formulation, then 15-25% (w/w) EBAAP was added to the mixture, and upon adding 1-10% (w/w) poloxamer to the same mixture, the resulting mixture was allowed to rest at +4° C. until poloxamer precipitated (approximately 24 hours). After poloxamer precipitated, the mixture was homogenized by the help of a homogenizer or a stirrer, and then upon adding 1-5% (w/w) sodium pentaborate pentahydrate, it was allowed to hydrate at +4° C. After jelling is completed, if considered necessary, sodium carbonate or citric acid can be used for neutralizing pH. The mixture became ready for use upon being allowed to rest at +4° C. for 24 hours. After formation of gelling, the composition of the invention is in gel form.

In the preparation of the gel of the present invention, sodium borate ($Na[B_5O_6(OH)_4] \cdot 3H_2O$) was especially preferred as the boron compound. Apart from this compound; borax, boric acid, alkaline and alkaline earth metal borates and all hydrate forms of these borates, ammonium borates, boric acid esters can also be used.

Antimicrobial Tests

Modified Disc Diffusion Method

Standard NCCLS disc diffusion method was used by being modified in order to determine the antimicrobial activity of boron compounds, EBAAP and the developed gel formulation on each microorganism that is being tested. The 100 µl solution including $10^8$ cfu/ml bacteria, $10^6$ cfu/ml yeast and $10^4$ spores/ml fungi was prepared with new cultures and inoculated with spreading method on Nutrient Agar (NA), Sabouraud Dextrose Agar (SDA) and Potato Dextrose Agar (PDA), respectively. 20 µl of sterile water was dropped on the empty discs and it was separately immersed into pulverized zinc borate, sodium borate, sodium perborate tetrahydrate, borax pentahydrate, disodium octaborate tetrahydrate. The discs coded with zinc borate, sodium borate, sodium perborate tetrahydrate, borax pentahydrate, disodium octaborate tetrahydrate were placed in inoculated petri dishes. Empty discs with 20 µl drop of sterile water were used as negative control. Furthermore, 19 µl empty discs were impregnated with EBAAP and antimicrobial activity tests were performed. Ofloxacin (10 µg/disc) and nystatin (30 µg/disc) were used as positive control for bacteria and fungi, respectively. The petri dishes, which were inoculated and on which modified disc diffusion method was applied, were incubated for 24 hours for bacteria and 48 hours for yeasts at 36±1° C., and for 72 hours for fungi at 25±1° C. Antimicrobial activity against microorganisms tested with modified disc diffusion method was assessed by measuring the inhibition zone (area where microorganisms do not grow). Antimicrobial activity test results of the tested boron compounds are summarized in Table 1 and 2. All tests were repeated at least twice.

Antiviral Tests

EBAAP Antiviral Activity Tests

In order to produce Human adenovirus type 5 Adenoid 75 strain and Poliovirus type 1 Chat strain virus and to carry out the experiment, a complete layer of HEp-2 cells (ATCC CCL-23), which are human monolayer tumor cells, were used. For determining virus titration, reference Human adenovirus type 5 Adenoid 75 strain and Poliovirus type 1 Chat strain were inoculated by making serial dilutions to HEp-2 cells, and by taking as basis the virus dilution that produces a cytopathic effect visible in invert microscope, virus titration was computed by using Spearman-Karber method. In order to determine sub-cytotoxic concentration of EBAAP, EBAAP was 10-fold serially diluted with Eagle's minimum essential medium (MEM) and non-toxic concentrations were detected in the cell medium and these concentrations were used in the experiment. For the controls, MEM inoculated HEp-2 cells, full layer HEp-2 cells wherein EBAAP was not added, 10-fold diluted reference virus titration control, formaldehyde control and controls containing toxic concentrations of EBAAP were used as negative control instead of the virus.

Preparation of Cell Culture Medium and the Chemicals

MEM medium: 10% serum (FBS) containing enzymes, hormones and growth factors for the cells to be able to cling to the surfaces and proliferate; and 40 IU/ml penicillin, 0.04 mg/ml streptomycin, 0.5 mg/ml glutamine to prevent fungi and bacteria contamination; and 1% Sodium Bicarbonate as a buffer solution were added therein.

FBS: Inactivated and mycoplasma-free

Sodium bicarbonate: Sterile 7.5% solution

Medium Used in Virus Inoculation: The medium included 1% antibiotic (Penicillin, Streptomycine, Amphotericin B) in order to prevent fungi and bacteria contamination, and 1% Sodium bicarbonate as a buffer solution. FBS serum is not added to this medium.

Preparation of Clean and Contaminated Media

Clean medium; 0.3 gr Bovine Serum Albumin Fraction V was dissolved in 100 ml sterile water. The solution that was obtained was sterilized by being passed through a filter with mesh size 0.22 µM.

Contaminated medium; Sheep Erythrocyte and BSA were used for the contaminated medium. 3 g BSA was dissolved in 100 ml sterile water and filtered. 3 ml sheep erythrocyte was completed to 97 ml BSA.

Erythrocyte; 8 ml fresh sheep blood was rotated at 800 G for 10 minutes and then its supernatant was removed. Upon adding 8 ml phosphate buffered saline (PBS) thereto, pipetting was performed and it was again rotated at 800 G for 10 minutes. This procedure was repeated 3 times.

Analysis:

Firstly, liquid EBAAP was solid serially diluted with the cell culture medium (MEM) and its non-toxic concentration in cell culture was calculated. 8 ml of the EBAAP that was to be tested was mixed with 2 ml hard water. The obtained solution was serially diluted (dilution step 1:10) with MEM. It was inoculated in 96-well monolayered cells. The microscopic changes that occurred were recorded. Concentrations that showed cytopathic effect (CPE) were determined. EBAAP and formaldehyde CPE values were compared. After determining non-toxic concentration of EBAAP on the cells, the effect of EBAAP on virus titration as a result of 5-60 minute separate application periods in clean and contaminated media was studied. For the controls, MEM inoculated HEp-2 cells, full layer HEp-2 cells wherein EBAAP was not added, 10-fold diluted reference virus titration control, formaldehyde control and controls containing toxic concentrations of EBAAP were used as negative control instead of the virus.

Taking as basis the virus dilutions wherein cytopathic effect that is visible in invert microscope is formed, virus titration was calculated as $TCID_{50}$ value by using Spearman-Karber method. Antiviral activity test results are summarized in Table 5, 6 and 7.

Antimicrobial Activity Tests of the Prepared Formulations;

Antimicrobial activity tests were performed for the compositions claimed to have antimicrobial and antiviral activity by means of the modified disc diffusion method. Modified disc diffusion experiments of the formulations were performed by providing wells on the medium and adding the developed formulation into the said wells. Antimicrobial activity test results are summarized in Table 3. Antiviral activity tests of the formulations were carried out by means of the above mentioned method. The test results are summarized in Table 6 and 7.

Experimental Results

Antimicrobial Test Results

Antimicrobial activity test results of the tested boron compounds are summarized in Table 1. All tests were repeated at least twice.

TABLE 1

Antimicrobial activity of Sodium Pentaborate Pentahydrate (SPP), Zinc borate (ZB), Borax (SB), Borax Pentahydrate (BP) and Disodium Octaborate Tetrahydrate (DOT) on the tested microorganisms

| | | Boron compounds | | | | |
|---|---|---|---|---|---|---|
| | Microorganisms | SPP | ZB | SB | BP | DOT |
| Bacteria | Escherichia coli | + | + | + | + | + |
| | Staphylococcus aureus | + | + | + | + | + |
| | Pseudomonas aeruginosa | + | + | + | + | + |
| | Klebsiella pneumoniae | + | + | + | + | + |
| | Acinetobacter baumannii | + | + | + | + | + |
| | Bacillus subtilis | + | + | + | + | + |
| | Methicillin-resistant Staphylococcus aureus (MRSA) | + | + | + | + | + |
| | Vancomycin-resistant Enterococcus(VRE) | + | + | + | + | + |
| Yeast | Candida albicans | + | + | + | + | + |
| Fungi | Aspergillus spp. | + | + | + | + | + |
| | Fusarium oxysporum | + | + | + | + | + |
| | Botrytis cinerea | + | + | + | + | + |
| | Penicillium spp. | + | + | + | + | + |

TABLE 2

Antimicrobial activity of EBAAP on the tested microorganisms

| | Microorganisms | EBAAP |
|---|---|---|
| Bacteria | Escherichia coli ATCC 25922 | − |
| | Staphylococcus aureus ATCC 29213 | + |
| | Pseudomonas aeruginosa ATCC 27853 | + |
| | Klebsiella pneumoniae ATCC 13883 | + |
| | Acinetobacter baumannii | + |
| | Bacillus subtilis ATCC 6633 | + |
| Yeast | Candida albicans | + |
| Fungi | Aspergillus niger | + |
| | Botrytis cinerae | + |
| | Fusarium oxysporum | + |
| | Penicillium vinaceum | + |

TABLE 3

Antimicrobial activity of the developed formulations on the tested microorganisms

| | Microorganisms | F 1 | F 2 |
|---|---|---|---|
| Bacteria | Escherichia coli ATCC 25922 | + | + |
| | Staphylococcus aureus ATCC 29213 | + | + |
| | Pseudomonas aeruginosa ATCC 27853 | + | + |
| | Klebsiella pneumoniae ATCC 13883 | + | + |
| | Bacillus subtilis ATCC 6633 | + | + |
| | Acinetobacter baumannii | + | + |
| | Methicillin-resistant Staphylococcus aureus (MRSA) | + | + |
| | Vancomycin-resistant Enterococcus(VRE) | + | + |
| Yeast | Candida albicans | + | + |
| Fungi | Aspergillus niger | + | + |
| | Botrytis cinerae | + | + |
| | Fusarium oxysporum | + | + |
| | Penicillium vinaceum | + | + |

Antimicrobial activities of the insect repellent composition of the present invention were tested by using bacteria (Escherichia coli, Staphylococcus aureus, Pseudomonas aeruginosa, Klebsiella pneumoniae, Bacillus subtilis, Acinetobacter baumannii, MRSA and VRE), yeast (Candida albicans) and fungus (Aspergillus niger, Botrytis cinerea, Fusarium oxysporum and Penicillium vinaceum) isolates. According to the obtained results; it was observed that the products containing boron compounds, EBAAP and/or hydrogen peroxide had antimicrobial activity on all of the tested microorganisms.

Antiviral Tests:

It was observed in the calculations made as a result of the test that EBAAP caused 2 log reduction at the end of 5 minutes and 4 log reduction at the end of 60 minutes in virus titer (Table 4 and Table 5) as a result of application at a ratio of 1/1, at room temperature (20° C.), in clean and contaminated media and with 5 and 60 minute application periods.

TABLE 4

Test results of antiviral activity of EBAAP against Adenovirus Type 5 (Av-5)

| AV-5 Virus titer* | | 5 minutes 6.0 | | 60 minutes 6.0 | |
|---|---|---|---|---|---|
| | | Clean medium | Contm. medium | Clean medium | Contm. medium |
| EBAAP | EBAAP virüs titer** | 4.0 | 4.0 | 2.0 | 2.0 |
| | Ratio of reduction in virus titer*** | 2.0 | 2.0 | 4.0 | 4.0 |

*Logarithmic $TCID_{50}$ value of the virus in ml.
**Logarithmic $TCID_{50}$ value of the virus treated with EBAAP at different periods and media.
***Logarithmic TCID50 ratio between the virus titer and the virus titer treated with EBAAP

TABLE 5

Test results of antiviral activity of EBAAP against Poliovirus Type 1 (PV-1)

| PV-1 Virus titer* | | 5 minutes 5.0 | | 60 minutes 5.0 | |
|---|---|---|---|---|---|
| | | Clean medium | Contm. medium | Clean medium | Contm. medium |
| EBAAP | EBAAP virus titer** | 3.0 | 3.0 | 1.0 | 1.0 |
| | Ratio of reduction in virus titer*** | 2.0 | 2.0 | 4.0 | 4.0 |

*Logarithmic $TCID_{50}$ value of the virus in ml.
**Logarithmic $TCID_{50}$ value of the virus treated with EBAAP at different periods and media.
***Logarithmic TCID50 ratio between the virus titer and the virus titer treated with EBAAP As a conclusion; these experiment results show that EBAAP is 99.9% active against AV-5 and PV-1 viruses when used directly without being diluted at room temperature (20° C.) as a result of a 60 minute application.

TABLE 6

Test results of antiviral activity of the composition with 3% poloxamer against Adenovirus Type 5 (Av-5)

| AV-5 Virus titer* | | 5 minutes 5.0 | | 60 minutes 5.0 | |
|---|---|---|---|---|---|
| | | Clean medium | Contm. medium | Clean medium | Contm. medium |
| 3% poloxamer gel | Jelli virus titer** | 2 | 2 | 1 | 1 |
| | Ratio of reduction in virus titer*** | 3 | 3 | 4 | 4 |

*Logarithmic $TCID_{50}$ value of the virus in ml.
**Logarithmic $TCID_{50}$ value of the virus treated with the gel at different periods and media.
***Logarithmic TCID50 ratio between the virus titer and the virus titer treated with the gel

TABLE 7

Test results of antiviral activity of the composition with 5% poloxamer against Adenovirus Type 5 (Av-5)

| AV-5 Virus titer* | | 5 minutes 5.0 | | 60 minutes 5.0 | |
|---|---|---|---|---|---|
| | | Clean medium | Contm. medium | Clean medium | Contm. medium |
| 5% poloxamer gel | Jelli virus titer** | 1 | 1 | 1 | 1 |
| | Ratio of reduction in virus titer*** | 4 | 4 | 4 | 4 |

*Logarithmic $TCID_{50}$ value of the virus in ml.
**Logarithmic $TCID_{50}$ value of the virus treated with the gel at different periods and media.
***Logarithmic TCID50 ratio between the virus titer and the virus titer treated with the gel These experimental results show that when the gel containing 3% poloxamer (composition 1) was applied directly at room temperature (20° C.), it was not active against AV-5 in 5 minutes while it was 99.9% active against AV-5 in an application period of 60 minutes. The results further show that when the gel containing 5% poloxamer (composition 1) was applied directly at room temperature (20° C.), it was 99.9% active against AV-5 in application periods of both 5 and 60 minutes.

Application of the Invention

The compositions of the present invention can be obtained as antimicrobial (antibacterial, anticandidal, antifungal) and antiviral lotions, creams, emulsions, sprays, foams, gelatins, pastes, powders or plasters, skin plates and wound dressing textile products in different therapeutic ratios.

All kinds of perfumes, moisturizers and surfactants, which will not chemically interact with the products, can be added to the said composition at suitable concentrations such that they will not reduce the antimicrobial and antiviral properties thereof.

By application of the present invention, antiviral activity prevents viral replication and prevents proliferation of the virus.

The composition of the present invention is suitable for use in many pharmacological areas such as applications of tablets, capsules, pastilles, drops, syrups, suppositories, gels, lotions, ampoules, tubes.

The prepared composition can be administered by all kinds of ways that enable body absorption such as by oral, nasal, ophthalmic, otic, local, ventricle, vaginal, rectal, dermal, intravenous, intramuscular, subcutaneous and intradermal route.

The product of the present invention can be used in all medical products, personal care products, cosmetic applications, drug formulations and medical applications upon being optimized.

The said invention can find use in all kinds of products in textile, electronic goods, automotive industry, medical sector, construction materials, agriculture, biomedical science, packaging, hygiene, food, industrial design, sports goods, energy industry, defense industry, and in all sectors wherein antimicrobial and antiviral activities are desired and biodegradation is desired to be controlled; and thus antimicrobial and antiviral products with a very broad spectrum can be obtained.

The invention claimed is:

1. An insect repellent composition, comprising poloxamer, a boron compound, ethyl butyl acetylaminopropionate and 1% (w/w) hydrogen peroxide, wherein the poloxamer is 5-15% (w/w), the boron compound is 1-5% (w/w), the ethyl butyl acetylaminopropionate is 15-25% (w/w), and the boron compound is sodium borate, wherein, the insect repellant composition is antimicrobial and antiviral, and the insect repellant composition exhibits antifungal activity on the fungi *Aspergillus niger, Botrytis cinerea, Fusarium oxysporum* and *Penicillium vinaceum*, and antimicrobial activity on VRE.

2. The insect repellent composition according to claim 1, wherein, the insect repellant composition exhibits antimicrobial activity on the bacteria *Escherichia coli, Staphylococcus aureus, Pseudomonas aeruginosa, Klebsiella pneumoniae, Bacillus subtilis, Acinetobacter baumannii*, and MRSA.

3. The insect repellent composition according to claim 1, wherein, the insect repellant composition exhibits anticandidal activity on the yeast *Candida albicans*.

4. The insect repellent composition according to claim 1, wherein, the insect repellant composition has antiviral activity against enveloped and non-enveloped DNA and RNA viruses.

5. The insect repellent composition according to claim 4, wherein, the insect repellant composition is in a form of tablets, capsules, pastilles, drops, syrups, suppositories, gels, lotions, ampoules, or tubes.

6. The insect repellent composition according to claim 5, wherein, the insect repellant composition is configured to be applied via oral, nasal, ophthalmic, otic, local, ventricle, vaginal, rectal, dermal, intravenous, intramuscular, subcutaneous or intradermal route.

\* \* \* \* \*